United States Patent
Yoshioka et al.

(10) Patent No.: US 6,555,225 B1
(45) Date of Patent: Apr. 29, 2003

(54) ION COMPLEX, COATED PRODUCT AND COATING METHOD

(75) Inventors: Hiroshi Yoshioka, Hadano (JP); Yuichi Mori, Yokohama (JP); Sunao Kubota, Kunitachi (JP)

(73) Assignees: M&M Laboratory Co., Ltd., Yamanashi (JP); Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/535,532

(22) Filed: Mar. 27, 2000

Related U.S. Application Data

(63) Continuation of application No. PCT/JP99/04021, filed on Jul. 27, 1999.

(30) Foreign Application Priority Data

Jul. 27, 1998 (JP) ............................................ 10-211008

(51) Int. Cl.⁷ ....................... B32B 27/28; C08L 101/12; C08L 101/14
(52) U.S. Cl. .................... 428/411.1; 428/500; 428/409; 427/2.1; 427/180; 427/189; 427/195; 427/336; 524/501; 524/514; 524/457; 524/460
(58) Field of Search ......................... 427/2.1, 180, 336, 427/189, 195; 428/500, 411.1, 409; 524/501, 514, 457, 460

(56) References Cited

U.S. PATENT DOCUMENTS 4,871,461 A * 10/1989 Karakane et al. ............ 210/638
4,876,126 A * 10/1989 Takemura et al. .......... 428/35.7
5,731,087 A * 3/1998 Fan et al. .................... 428/212

FOREIGN PATENT DOCUMENTS

| | | |
|---|---|---|
| EP | 0 544 259 A1 | 6/1993 |
| JP | 54-147696 | 11/1979 |
| JP | 60-139743 * | 7/1985 |
| JP | 63-59966 | 3/1988 |
| JP | 63-214304 | 9/1988 |
| JP | 64-75508 | 3/1989 |
| JP | 2-298902 | 12/1990 |
| JP | 7-33682 | 2/1995 |
| JP | 8-198906 | 8/1996 |
| JP | 10-287711 | 10/1998 |

OTHER PUBLICATIONS

Derwent Abstract of WO 200029490, May 2000.*
Derwent Publications Ltd., abstract, AN 1978–16542A & JP 53 004788 A, Jan. 17, 1978.
Derwent Publications Ltd., abstract, AN 1988–180719 & JP 63 119774 A, May 24, 1988.
Patent Abstracts of Japan, vol. 9, No. 293, Nov. 20, 1985 & JP 60 135432 A, Jul. 18, 1985.

* cited by examiner

Primary Examiner—D. Lawrence Tarazano
(74) Attorney, Agent, or Firm—Pillsbury Winthrop LLP

(57) ABSTRACT

An ion complex which comprises a water-insoluble polyion (P) and a water-soluble polyion (A); and is insoluble in water and soluble in an aqueous organic solvent. Such an ion complex becomes a coating material which can preferably be used for coating of various ionic substances (e.g., substance having biological activity such as an anticoagulant property or an antibacterial property).

15 Claims, No Drawings

ION COMPLEX, COATED PRODUCT AND COATING METHOD

RELATED APPLICATION

This is a continuation application of International application No. PCT/JP99/04021 filed on Jul. 27, 1999 for ION COMPLEX, COATED PRODUCT AND COATING METHOD.

BACKGROUND OF THE INVENTION

1. Filed of the Invention

The present invention relates to a (poly)ion complex which has an excellent characteristic in that it is insoluble in water but is soluble an aqueous (or water-containing) organic solvent. The ion complex according to the present invention is suitably usable for the coating of various kinds of base materials or substrates (such as biomedical material) with various kinds of ionic substances (e.g., a biologically or a physiologically active substance such as an anticoagulant or an antibacterial agent) by utilizing this characteristic, although it is difficult to effect such a coating while allowing the ionic substance to effectively exhibit its function.

2. Related Background Art

An ion complex or coating material, a coated product based on the ion complex, or a coating method according to the present invention are applicable without particular limitation to the field of coating of the surface of various kinds of base materials or substrates, especially to a field wherein the formation of a coating having an excellent coating property is required while causing such a complex to exhibit the function of the ionic component constituting the complex (e.g., fields such as medical use, electronic materials, and antistatic materials). However, at first, there will be described a background art relating to an embodiment of the ion complex according to the present invention to which not only a coating property but also an anticoagulant property has been imparted.

When blood comes into contact with an artificial material other than a living organism, the blood coagulation system is activated, by the surface of the material, to cause blood coagulation. The problem of such blood coagulation seriously hinders the development of therapeutic and diagnostic instruments or devices which are to come in contact with blood, and the development of an excellent anticoagulant material has been desired. With respect to the anticoagulant material, various kinds of surface structures and surface treating methods have been proposed but, at present, it is considered that heparinized materials show the best anticoagulant properties.

Heparin is an anticoagulant substance originated from a living organism and is a mucopolysaccharide having negative electric charges based on a large number of sulfuric acid groups thereof. The heparinizing methods which have conventionally been investigated are roughly classified into the following three types.

1) Simple blending method: A method wherein heparin is simply mixed into a resin. For example, it is said that a material which has been obtained by mixing heparin into an epoxy resin by using this method shows a good anticoagulant property. However, there is no bonding between such a polymer matrix and the heparin, and therefore the heparin is easily lost from the polymer matrix in blood, and there is a defect that the anticoagulant property thereof cannot be maintained for a long period of time.

2) Covalent bonding method: A method wherein heparin is chemically fixed, on the surface of a material to be coated, by covalent bonding by utilizing the functional group of the heparin. However, the quantity of the heparin which can be fixed by this method is about 0.1 $\mu g/cm^2$ at the maximum. In addition, the heparin is denatured by the chemical reaction, or the heparin is not released from the material to be coated, and therefore the resultant anticoagulant activity of the above material is insufficient, and at present, a satisfactory anticoagulant material has not been obtained yet.

3) Ionic bonding method: A method wherein heparin is electrostatically fixed on the surface of a material having positive charges by utilizing the negative charges of the heparin. It is said that this method imparts the best anticoagulant property to such a material.

As for the ionic bonding method, the following methods are known:

(a) A method wherein a quaternary ammonium salt-type surfactant such as benzalkonium chloride (BC) or tridodecylmethylammonium chloride (TDMAC) is adsorbed onto the surface of a material to be coated, and positive charges are introduced into the surface of the material; and (b) A method wherein the surface of a material to be coated is coated with a water-insoluble polycation having a quaternary ammonium group in its main chain or side chain, and positive charges are introduced into the surface of the material.

In the above-mentioned method (a), the hydrophobic group of the TDMAC or BC is adsorbed onto the surface side of the material to be coated, and the hydrophilic quaternary nitrogen thereof is oriented toward the outside of the TDMAC or BC, whereby positive charges of high density can be introduced onto the material surface two-dimensionally. Accordingly, when such a surface is caused to contact an aqueous heparin solution, the heparin can be bonded to the surface of the material to be coated through ionic bonding.

Further, it is known that the ion complex of the TDMAC and heparin is soluble in some organic solvents, and the ion complex can be subjected to coating by using a solvent casting method (Atha, D., et al., Proc. Nat. Acad. of Sci., 81, 1030–1034 (1984)).

However, when the heparin-coated material obtained by the above-mentioned method (a) is actually used in blood, the BC and TDMAC which have been adsorbed onto the surface of the material to be coated are low-molecular substances and therefore there is produced a defect that these substances are dissolved into blood together with the heparin. When such a cationic surfactant is dissolved into blood, the cationic surfactant causes a problem such as hemolysis and agglomeration of plasma protein. Further, there is also a problem that when such a heparin-coated material is used, the heparin is bonded only to the surface portion thereof, and therefore the heparin flows out at an early stage.

It has also been proposed that in order to suppress the above-mentioned dissolution of the TDMAC, the ion complex of TDMAC and heparin is subjected to coating and thereafter the resultant product is irradiated with gamma rays to crosslink the TDMAC (U.S. Pat. No. 5,441,759). However, there is a fear that irradiation with gamma rays deteriorates the material to be coated.

On the other hand, as a product based on the above method (b), there is known "Anthron" (trademark, mfd. by Toray Industries, Inc.) as a material showing a good anticoagulant property. This material has been obtained by synthesizing a graft copolymer comprising a main chain of polyvinyl chloride, and a side chain bonded thereto comprising a random copolymer of a cationic monomer and a hydrophilic monomer; and then causing a coating layer which has been formed by using such a graft copolymer in advance, to occlude heparin thereinto. This material shows an anticoagulant property based on the slow release of heparin at a rate of 0.01 unit/cm$^2$·min or more, when it is in contact with blood (Mori, Y., et al., Trans. Am. Soc. Artif. Intern. Organs, 24, 736 (1978)).

In the heparin-coated material obtained by this method, the dissolution of a substance other than heparin is suppressed. However, in this method, it is necessary that the surface of a material is coated with the water-insoluble polycation, in advance, by a solvent casting method, etc., and the solvent is evaporated, and thereafter the resultant product is immersed in a high-concentration aqueous heparin solution for a long period of time to form a complex thereof with the heparin. Such a process has a problem that it requires much labor and a long period of time, and further it must use an excess of expensive heparin.

Further, the inventor's research group has already disclosed a heparinized material characterized in that an ion pair of heparin and a polymer of a quaternary ammonium salt monomer having a polymerizable functional group and a hydrocarbon chain with a carbon number of not less than 10 and less than 30 is adsorbed onto a surface which is to be in contact with blood (Japanese Patent Application No. Hei. 6-162120, KOKAI (Japanese Unexamined Patent Publication) No. Hei. 7-265405). In this case, when the cationic surfactant is polymerized, the dissolution thereof can be prevented. However, similarly as in the case of the above TDMAC, the ion pair of the cationic monomer and heparin is soluble in an organic solvent, but the ion complex of polycation and heparin which has been obtained by the polymerization of the cationic monomer is insoluble in any kind of solvent, and therefore it has been impossible to effect coating by using a solvent casting method.

SUMMARY OF THE INVENTION

An object of the present invention is to provide an ion complex which solves the above-mentioned problems encountered in the prior art.

Another object of the present invention is to provide an ion complex which is insoluble in water and is soluble in aqueous organic solvent.

A further object of the present invention is to provide a coating material which is suitably usable for the coating (e.g., coating of a biomedical material) with various kinds of ionic substances (e.g., substances having a biological activity such as anticoagulant or antibacterial property), a coated product or coating method based on such a coating material.

DISCLOSURE OF INVENTION

As result of earnest study, the present inventors have found an ion complex comprising a water-insoluble polyion (P) and a water-soluble polyion (A), which is water-insoluble and is soluble in an aqueous (or water-containing) organic solvent.

As result of further study, the present inventors have also found that the ion complex having the above-mentioned property has an excellent characteristic as a coating material for various kinds of ionic substances and is extremely effective in solving the above-mentioned problems encountered in the prior art.

The ion complex according to the present invention is based on the above discovery, and comprises a water-insoluble polyion (P) and a water-soluble polyion (A); the ion complex being insoluble in water and soluble in an aqueous organic solvent.

The present invention also provides a coated product comprising a material to be coated, and a coating layer covering at least a portion of the surface of the material to be coated, wherein the coating layer comprises an ion complex which comprises a water-insoluble polyion (P) and a water-soluble polyion (A); and is insoluble in water and soluble in an aqueous organic solvent.

The present invention further provides a coating method comprising:

forming on a material to be coated a layer of a solution comprising an aqueous organic solvent and an ion complex dissolved in the solvent; and evaporating the aqueous organic solvent to form on the material to be coated a coating layer comprising the ion complex;

wherein the ion complex comprises a water-insoluble polyion (P) and a water-soluble polyion (A); and the ion complex is insoluble in water and soluble in an aqueous organic solvent.

The present invention further provides a coating method comprising:

attaching a coating material in the form of powder comprising an ion complex to a material to be coated;

swelling the ion complex with an aqueous organic solvent; and evaporating the aqueous organic solvent to form, on the material to be coated, a coating layer comprising the ion complex;

wherein the ion complex comprises a water-insoluble polyion (P) and a water-soluble polyion (A); and the ion complex is insoluble in water and soluble in an aqueous organic solvent.

In general, it is known that a polyelectrolyte complex comprising a polycation and a polyanion (usually, referred to as "(poly)ion complex" or "polyelectrolyte complex") forms an aggregate which is insoluble in any kind of solvent due to its strong intermolecular interaction (E. Tsuchida and K. Abe, "Interaction between Macromolecules in Solution and Intermacromolecular Complexes", Springer-Verlag, 1982).

Accordingly, heretofore, it is practically impossible to subject such an ion complex to a coating operation by using a solvent and, accordingly, the practical use of the conventional ion complex encounters various difficulties. For example, in the production of the conventional heparinized material represented by the above-mentioned "Anthron" (registered trademark) as an anticoagulant material, a step of coating a material to be coated with a polycation by a solvent casting method using an organic solvent, etc., and another step of causing heparin as a polyanion in the form of an aqueous solution thereof to be adsorbed onto the surface of the material to be coated to which the above polycation has been fixed by coating must be separated.

On the other hand, the ion complex comprising a water-soluble polyion (A) and a water-insoluble polyion (P) according to the present invention has a characteristic such that it is insoluble in water but is soluble in an aqueous organic solvent. Accordingly, such an ion complex can easily be subjected to coating (such as solvent casting) on various base materials or substrates, and is applicable to the surface of a wide range of base materials or substrates (e.g., medical devices) comprising various material.

In addition, the problems encountered in the conventional coating material (e.g., a heparinized material) are solved by utilizing the ion complex according to the present invention. That is, a water-soluble polyion (A) such as polyanion (e.g., heparin) having an anticoagulant property, and polycation (e.g., polymyxin B) having an antibacterial property can be electrostatically fixed stably into a surface layer of various base materials or substrates.

Further, when such a coating surface comes into contact with aqueous fluid (e.g., body fluid such as blood), it is possible to slowly release the water-soluble polyion (A) (such as polyanion having an anticoagulant property and polycation having an antibacterial property) into the aqueous fluid, while effectively suppressing the dissolution of a coating component other than the water-soluble polyion (A).

In addition, in the ion complex according to the present invention, the water-soluble polyion (A) forms a (poly)ion complex with the water-insoluble polyion (P), and therefore it is also possible to stably sustain the function possessed by the complex (such as biological activity) for a long period of time while relatively suppressing the dissolution of the water-soluble polyion.

Further, in the ion complex according to the present invention, an ion complex of the water-soluble polyion (A) and the water-insoluble polyion (P) is formed in advance, and therefore it is possible to control the quantity of the functional material in the ion complex (polyion (A) and/or polyion (P); e.g., biologically active substance) precisely and arbitrarily.

In the present invention, the polyion complex with the water-soluble polyion (e.g., polyion having a biological activity such as heparin or an aminoglycoside-type antibiotic) is characterized in that it is insoluble in water, is insoluble in an organic solvent, but is soluble in an aqueous organic solvent. On the other hand, for example, the ion complex with heparin in the Japanese Patent No. 2131838 is characterized in that it is insoluble in water and is soluble in an organic solvent. Based on the difference in the character of the polyion complex with such a water-insoluble polyion, the water-soluble polyion (biologically active substance such as heparin) is slowly released from the polyion complex according to the present invention, as described hereinafter. On the other hand, in the case of the above-mentioned polyion complex of Japanese Patent No. 2131838, it is said that the polyion complex is characterized in that the dissolution of heparin from the polyion complex is suppressed as completely as possible.

For example, in a case where an anticoagulant material or antibacterial material is designed by using a polyion complex which has been constituted by a polyion having a biological activity as one component thereof, it is considered that the most important factor for exhibiting the function of the polyion complex is that the polyion having the biological activity is slowly released from the polyion complex into the body fluid such as blood.

For example, it is considered that the function of heparin, a polyanion as a typical anticoagulant, is that it forms a complex with antithrombin III in blood and promotes the inhibition of various blood coagulation factors (serine protease) so as to exhibit an anticoagulant activity. Accordingly, heparin is a polyanion which does not exhibit its strong anticoagulant function until it is dissolved into blood (e.g., "Kagaku no Ryoiki (Area of Chemistry)-Structures and Functions of Mucopolysaccharide", Extra number No. 83, 1968 may be referred to).

On the other hand, it is considered that the function of the aminoglycoside antibiotic, as a polycation having an antibacterial property, is that the aminoglycoside antibiotic having a basic group forms ionic bonds with the cell membrane of bacteria having acidity, and then is incorporated into the cell and is combined with ribosome, whereby the function is exhibited due to the inhibition of protein syntheses, harm to the cell membrane and the inhibition of DNA replication, etc. Similar to the case of heparin, the aminoglycoside antibiotic does not exhibit its strong antibacterial activity until it is dissolved into the body fluid such as blood (e.g., Gendai Kagaku (Chemistry Today), Extra Number No. 9, "Advanced Studies of Antibiotics", published by Tokyo Kagaku Dojin, 1987 may be referred to).

As described above, the biological activity of the polyion such as heparin and antibiotics is not exhibited until the polyion is dissolved into the blood or body fluid, and therefore it is the most important point of the design of such a biologically active material to cause the biologically active material to exhibit slow release thereof in a controlled manner.

In the present invention, in order to slowly release the water-soluble polyion (A) having a biological activity from the polyion complex into the blood or body fluid through a controlled process, it is preferred that the polyion (A) is bonded to the water-insoluble polyion (P) with relatively weak bonding. That is, it is preferred that not all of the ionic groups of the polyion (A) form binding pairs with the ionic groups of the water-insoluble polyion (P), and a portion of the ionic groups of the polyion (A) remain in the free state thereof without forming binding pairs.

The feature of the polyion complex according to the present invention, wherein a portion of the ionic groups of the polyion (A) remain in the free state thereof without forming binding pairs, can be explained on the basis of a phenomenon such that the polyion complex is insoluble in water or an organic solvent (such as ethanol), but is soluble in an aqueous organic solvent as described hereinabove. That is, a portion of the ionic groups of the polyion (A) forming binding pairs with the ionic groups of the polyion (P) are soluble in an organic solvent (such as ethanol), and a portion of the polyion (A) having free ionic groups is soluble in water. Accordingly, it is necessary to use an aqueous organic solvent comprising a mixture of water and an organic solvent in order to simultaneously dissolve the bonding pair-forming portion and the free portion which are copresent in the above polyion complex.

On the other hand, when the polyion complex is dissolved in an organic solvent (such as ethanol), it is considered that most of the ionic groups of the polyion (A) form binding pairs with the ionic groups of the polyion (P), and the polyion (A) having the biological activity is not substantially dissolved into blood or body fluid, whereby the biological activity of the polyion complex remains at a very low level.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

Hereinbelow, the present invention will be described in detail with reference to the accompanying drawings as desired. In the following description, "part(s)" and "%"representing proportion or ratio are those based on weight, unless otherwise noted specifically.

(Ion Complex)

The ion complex according to the present invention is an ion complex which comprises a water-insoluble polyion (P) and a water-soluble polyion (A), and is insoluble in water and soluble in an aqueous (or water-containing) organic solvent.

In the present invention, the formation of the above "ion complex" can be confirmed, e.g., in the following manner. Herein, the conditions to be used for the confirmation of the presence or solubility (insolubility) for such a purpose are only applicable to these confirmation, etc., and they do not limit the other portions of the present invention (e.g., conditions for the production and use of polyion and ion complex). The following confirmation of the presence or solubility (insolubility) is to be conducted under a neutral condition of pH=7, unless otherwise noted specifically.

<Confirmation of presence of ion complex>

The presence of an ion complex can be confirmed by the fact that a sample to be examined is not substantially dissolved when it is immersed in a large excess of distilled water, and that the sample (the water-soluble component constituting the complex) is dissolved when it is immersed in an aqueous NaCl solution having a concentration of 2M (mol/liter).

On the other hand, a simple (non-ion complex) polyanion, polycation, or poly-ampholytic ion shows that either it is dissolved in any of distilled water and the above-mentioned aqueous NaCl solution (when it is water-soluble), or it is not dissolved in distilled water nor the above-mentioned aqueous NaCl solution (when it is water-insoluble). Herein, in the case of a sample (not forming an ion complex) mixture of a water-insoluble polyion and a water-soluble polyion, it is dissolved in both of distilled water and the above-mentioned aqueous NaCl solution.

<Confirmation of Insolubility in Distilled Water>

A fact that a sample to be examined (such as ion complex) is not dissolved in distilled water can be confirmed, e.g., in the following manner.

Thus, about 1 g (represented by the weight thereof=$W_1$g) of the sample to be examined is weighed out, and is immersed in about one liter of distilled water at 25° C. and is left standing as it is for 24 hours. Thereafter, the sample is dried in a vacuum dryer at 0.1 torr at 40° C. for 24 hours. In a case where the weight of the sample to be examined after the drying is represented by $W_2$g, in the present invention, the sample is judged to be "insoluble in distilled water" when the value of $(W_1-W_2)/W_1$ is 0.1 or less. The value of such $(W_1-W_2)/W_1$ may preferably be 0.05 or less (more preferably 0.01 or less).

A fact that the ion complex according to the present invention is "water-insoluble" can also be confirmed by the above-mentioned fact that it is insoluble in distilled water.

<Confirmation of Solubility in Aqueous NaCl solution>

A fact that a sample to be examined (such as ion complex) is soluble in an aqueous NaCl solution can be confirmed, e.g., in the following manner.

Thus, about 1 g (represented by the weight thereof=$W_3$g) of a sample to be examined is weighed out, and is immersed in about one liter of an aqueous NaCl solution having a concentration of 2M at 25° C., and is left standing as it is for 48 hours. Thereafter, the sample is washed with distilled water and dried in a vacuum dryer at 0.1 torr at 40° C. for 24 hours. In a case where the weight of the sample to be examined after the drying is represented by $W_4$g, in the present invention, the sample is judged to be "soluble in aqueous NaCl solution" when the value of $(W_3-W_4)/W_3$ is 0.01 or more. The value of such $(W_3-W_4)/W_3$ may preferably be 0.02 or more (more preferably 0.05 or more).

<Confirmation of Substantial Insolubility in Organic Solvent>

A fact that the polyion complex according to the present invention is substantially insoluble in an organic solvent such as ethanol, DMSO and THF (preferably, ethanol) can be confirmed, e.g., in the following manner.

Thus, about 1 g (represented by the weight thereof=$W_7$g) of sample to be examined (such as polyion complex) is weighed out, and is immersed in about 100 ml of an organic solvent at 25° C. and is left standing as it is for 24 hours. Thereafter, the sample is dried in a vacuum dryer at 0.1 torr at 40° C. for 24 hours. In a case where the weight of the sample to be examined after the drying is represented by $W_8$g, in the present invention, the sample is judged to be "insoluble in the organic solvent", when the value of $(W_7-W_8)/W_7$ is 0.1 or less. The value of such $(W_7-W_8)/W_7$ may preferably be 0.08 or less, more preferably 0.05 or less (particularly 0.03 or less).

<Confirmation of Solubility in Aqueous Organic Solvent>

A fact that a sample to be examined (such as ion complex) is soluble in an aqueous organic solvent can be confirmed, e.g., in the following manner.

Thus, about 1 g (represented by the weight thereof=$W_5$g) of sample to be examined is weighed out, and is immersed in about one liter of an aqueous ethanol (a mixture liquid of 82% of ethanol and 18% of water) at 25° C. and is left standing as it is for 48 hours. Thereafter, the sample is washed with distilled water, and is dried in a vacuum dryer at 0.1 torr at 40° C. for 24 hours. In a case where the weight of the sample to be examined after the drying is represented by $W_6$g, in the present invention, the sample is judged to be "soluble in aqueous organic solvent", when the value of $(W_5-W_6)/W_5$ is 0.3 or more. The value of such $(W_5-W_6)/W_5$ may preferably be 0.5 or more (more preferably 0.8 or more).

(Water-insoluble Polyion)

The water-insoluble polyion (P) to be used in the present invention is a molecule having at least two or more ionic groups in one molecule thereof. The polyion forms a stable ion complex with another water-soluble polyion satisfying a certain condition (e.g., a water-soluble polyion, as a whole molecule, having an electric charge of a sign opposite to that of the water-insoluble polyion) on the basis of its electric or steric characteristic, etc. In the present invention, the water-insoluble polyion (P) can be used without particular limitation, as long as it can form, with a water-soluble polyion (A), an ion complex which is water-insoluble and is soluble in an aqueous organic solvent.

The solubility of the water-insoluble polyion (P) in water (distilled water) may preferably be 1% or less, more preferably 0.1% or less (particularly 0.01% or less) at 37° C., when the total weight of the polyion and water is represented by 100%.

The molecule weight of the water-insoluble polyion (P) is not particularly limited, but it may preferably be in the range of $1\times10^4-100\times10^4$, more preferably $2\times10^4-60\times10^4$ (particularly $3\times10^4-30\times10^4$) in terms of weight average molecule weight (Mw) by gel permeation chromatography (GPC). In the determination of Mw by GPC used in this specification, dimethylformamide containing 10 mM of LiBr is used as a solvent, and standard polyethylene glycol (PEG) is used as standard substance for the molecule weight.

When the molecule weight Mw is less than $1\times10^4$, the formation of an ion complex with the water-soluble polyion (A) tends to be insufficient. On the other hand, when the molecule weight Mw exceeds $100\times10^4$, the tendency that the solubility of the ion complex in an aqueous organic solvent is decreased is further strengthened, and the solvent coating becomes difficult.

As described above, there is known a complex of a mono-cation and a polyanion, such as combination of heparin with BC and TDMAC, which becomes soluble in an organic solvent. However, the conventional ion complex comprising a water-insoluble polyion and a water-soluble polyion is insoluble in any kind of solvent. On the other hand, the ion complex according to the present invention has an important feature that it is insoluble in water, but is soluble in an aqueous organic solvent, as described above.

(One Embodiment of Method of Synthesizing Water-insoluble Polyion)

In the present invention, the water-insoluble polyion (P) is not particularly limited, as long as it can form an ion complex with the water-soluble polyion (A), which is water-insoluble and is soluble in an aqueous organic solvent. However, one which has been synthesized by the following method is suitably usable as the water-insoluble polyion (P).

That is, there is suitably usable a polyion which has been obtained by the copolymerization in an aqueous organic solvent, in the presence of a water-soluble polyion (A) dissolved therein, of a polymerizable monomer (B) having an electric charge of the sign opposite to that of the above polyion, with a monomer (C) for providing the water-insoluble polymer (P).

According to the present inventors' study, it has been found that an ion complex formed by a method wherein a random copolymer of a monomer (B) and a monomer (C) is synthesized in advance, and the resultant product is mixed with polyion (A) becomes insoluble in any kind of solvent, in the same manner as in the conventional ion complex. On the other hand, according to the present inventors' study, it has been found that when in an aqueous organic solvent, in the co-presence of a water-soluble polyion (A) dissolved therein, a polymerizable monomer (B) having an electric charge of the sign opposite to that of the polyion (A) is copolymerized with a monomer (C) for providing the water-insoluble polymer (P) and the resultant ion complex is soluble in an aqueous organic solvent.

According to the present inventors' knowledge, under the polymerization conditions for one embodiment of the present invention as described above, the copolymerization reaction proceeds under a state under which the monomer (B) is non-uniformly concentrated in the neighborhood of the polyion (A) on the basis of the co-presence of the polyion (A) having a sign opposite to that of the polymerizable monomer (B) in the copolymerization system of the monomer (B) and the monomer (C) for providing the water-insoluble polymer (P). At this time, the mixture of the polyion (A) and the monomer (B) is also soluble in an aqueous solution having a low salt concentration (NaCl of 0.1M or less), and, therefore, the mixture does not form a strong one-to-one ion pair, and it is difficult to isolate the ion pair of the polyion (A) and monomer (B). However, when the monomer (B) is polymerized to be formed into a polyion, a strong ion pair between the polyanion and the polycation is formed. It is presumed that the thus obtained copolymer does not become a random copolymer wherein the monomer (B) and the monomer (C) are statistically randomly arranged, but there is obtained a block copolymer wherein the block of the monomer (B) concentrated by the polyion (A) is connected to the block mainly comprising the monomer (C).

According to the present inventors' knowledge, it is presumed that the block of the water-insoluble polymer obtained by the above procedure which is rich in the monomer (B) forms an ion complex with the polyion (A), and the blocks mainly comprising the monomer (C) are connected to the both ends thereof, and therefore such a connection suppresses the aggregation thereof with another ion complex portion comprising the polyion (A) and the monomer (B). In other words, it is presumed that the ion complex portions comprising the block rich in the monomer (B) and the polyion (A) are separated with each other by the blocks mainly comprising the monomer (C), whereby the ion complex comprising the water-soluble polyion (A) and the polyion (P) comprising the monomer (B) and the monomer (C) becomes soluble in an aqueous organic solvent.

(Aqueous Organic Solvent)

As the organic solvent constituting the "aqueous organic solvent" in the present invention, it is possible to use an organic solvent having a compatibility with water without particular limitation. As the organic solvent, it is particularly preferred to use one which can be mixed with water in an arbitrary ratio, from a viewpoint such that it does not cause a phase separation even when the solvent composition is changed at the time of the evaporation of the solvent.

As such an organic solvent, e.g., there are suitably usable alcohols such as ethanol, methanol and isopropanol; ketones such as acetone and methyl ethyl ketone; tetrahydrofuran (THF), acetonitrile, dimethylformamide (DMF), dimethyl sulfoxide (DMSO), etc.

In the present invention, for example, it is possible to use an aqueous organic solvent as a solvent for the coating of a biologically active material comprising an ion complex, or as a polymerization solvent for the water-insoluble polyion (P). However, the compositions of these solvents are not necessarily the same.

(Coating Solvent)

When an aqueous organic solvent is used as a coating solvent, the kind of the organic solvent can appropriately be selected depending on the material to be coated. The denaturation or deformation of the material to be coated can be avoided by selecting a solvent which does not substantially dissolve the material to be coated. On the other hand, the adhesive property between the coating material and the material to be coated can be improved by selecting a solvent which dissolves the material to be coated to a certain extent.

The water content of the aqueous organic solvent can appropriately be set in a certain range wherein the solvent dissolves the coating material comprising the ion complex. However, the water content may preferably be as low as possible so as to avoid the precipitation of the ion complex due to a change in the solvent composition at the time of the evaporation of the solvent after the coating. More specifically, the water content may preferably be 5–60 wt. %, more preferably 15–40 wt. % (particularly 5–20 wt. %), when the total weight of the water and the organic solvent is represented by 100%.

In the present invention, the aqueous organic solvent may also contain a neutral salt of strong electrolyte, but the content thereof may preferably be as low as possible. More specifically, the content of the strong electrolyte may preferably be 5 wt. % or less, more preferably 1 wt. % or less (particularly 0.1 wt. % or less), when the total weight of the aqueous organic solvent and the strong electrolyte of neutral salt is represented by 100%. When the content of the strong electrolyte neutral salt exceeds 5 wt. %, there is strengthened a tendency that the ion complex causes a phase separation to be precipitated, or the electrostatically bonded ion complex is dissociated, whereby the fixation of the polyion (P) or (A) tends to become unstable.

(Polymerization Solvent)

When the aqueous organic solvent is used as the polymerization solvent for the water-insoluble polyion (P), polymerization is conducted under a condition under which the water-soluble polyion (A) is dissolved, and therefore it is sufficient to appropriately select the composition of the aqueous organic solvent depending on the solubility or concentration of the water-soluble polyion (A). When the water content of the aqueous organic solvent becomes high, the solubility of the water-soluble polyion (A) also becomes high, and therefore it is possible to conduct the polymerization reaction in the co-presence of the water-soluble polyion (A) at a high concentration. On the other hand, in such a case, a tendency that the solubility of the ion complex to be formed becomes low is strengthened, the polymerization reaction becomes a heterogeneous system so as to lower the molecular weight of the resultant polymer, and the molecular weight distribution is broadened, whereby the production of a coating material having a good film-forming property tends to become relatively difficult. Accordingly, when the aqueous organic solvent is used as the polymerization solvent for the water-insoluble polyion (P), the water content thereof may preferably be in the range of 10–80 wt. % in usual, more preferably 40–70 wt. %. (particularly 50–65 wt. %).

(Water-Soluble Polyion)

The Water-soluble polyion (A) in the present invention is a molecule having at least two or more ionic groups in one molecule thereof. In the present invention, the water-soluble polyion (A) can be used without particular limitation, as long as it can form an ion complex with the above-mentioned water-insoluble polyion (P), which is insoluble in water and is soluble in the aqueous organic solvent.

The solubility of the water-soluble polyion (A) in water (distilled water) may preferably be 1% or more, more preferably 5% or more (particularly 10% or more) at 37° C., when the total weight of the polyion and water is represented by 100%.

The molecular weight of the water-soluble polyion (A) is not particularly limited, but it may preferably be in the range of $200-1000 \times 10^4$, more preferably $1000-100 \times 10^4$ (particularly $1 \times 10^4 - 10 \times 10^4$, in terms of weight-average molecular weight (Mw) by GPC.

As long as it is water-soluble, the water-soluble polyion (A) may be any of a polyanion (referred to as one having a negative electric charge as the whole molecule thereof; in the same manner as in the description appearing hereinafter), a polycation (referred to as one having a positive electric charge as the whole molecule thereof; in the same manner as in the description appearing hereinafter) and an ampholite electrolyte; and can be any of a synthetic product, a semi-synthetic product, and a natural product without particular limitation. When a biological activity is imparted to the ion complex according to the present invention, it is preferred to impart the biological activity to at least one of the above-mentioned water-insoluble polyion (P) and the water-soluble polyion (A). In view of ease of exhibiting a higher biological activity, it is preferred to use one having a biological activity as the water-soluble polyion (A).

The biological activity which can be possessed by the water-soluble polyion (A) is not particularly limited. Examples thereof may include, e.g., an anticoagulant property, an antibacterial property, a cell growth property, an anti-cancer property, etc. (Polyanion having biological activity).

As the polyanion having a biological activity, for example, as one having an anticoagulant property, it is possible to use a copolymer of acrylic acid and 2-acrylamide-2-methylpropanesulfonic acid disclosed in KOKAI No. Hei. 8-191888, and various kinds of sulfonated polysaccharides such as dextran sulfate. As the polyanion having an anticoagulant property, it is particularly preferred to use heparin as one of natural mucopolysaccharides.

As the polyanion having an antibacterial property as its biological activity, it is possible to exemplify antibiotics having plural acidic groups such as penicillin-N, cephalosporin C, and cephabacin. As the polyanions having another biological activity, it is possible to exemplify nucleic acids such as DNA and RNA; acidic polysaccharides such as alginic acid and hyaluronic acid; acidic proteins such as collagen and albumin.

(Polycation Having Biological Activity)

As the polycation having a biological activity, it is possible to exemplify aminoglycoside-type antibiotics such as kanamycin, gentamycin and neomycin; cationic organic-type antibacterial substances such as chlorhexidine hydrochloride (Hibitane), and polymyxin B; and basic polysaccharides such as chitosan.

(Polymerizable Cationic or Anionic Monomer)

The polymerizable monomer (B) having an electric charge of a sign opposite to that of the water-soluble polyion (A) can be used without particular limitation, as long as it is a monomer which has a polymerizable functional group and a group capable of forming an ion pair with the water-soluble polyion (A), and is soluble in an aqueous organic solvent, but it may preferably be a water-soluble monomer with a small steric hindrance. Examples of the polymerizable functional group may include vinyl group, (meth)acrylic group, (meth)acrylamide group, etc. Examples of the group which can form an ion pair with the water-soluble polyion (A) may include cationic groups (such as primary, secondary, tertiary or quaternary nitrogen group, etc.) or anionic groups (such as carboxyl group, sulfonic acid group, phosphoric acid group, etc.).

As the polymerizable cationic monomer, it is also possible to use a polymerizable cationic surfactant having a long-chain alkyl group disclosed in KOKAI No. Hei. 7-265405, but in view of the polymerizable property thereof, it is preferred to use a cationic monomer with a small steric hindrance rather than such a cationic monomer having a group with a large steric hindrance. Preferred examples of such a cationic monomer with a small steric hindrance may include water-soluble cationic monomers such as dimethylaminoethyl (meth)acrylate and quaternary products thereof, dimethylaminopropyl (meth)acrylamide and quaternary products thereof, and vinyl pyridine and quaternary products thereof. On the other hand, examples of the polymerizable anionic monomer may include (meth)acrylic acid, itaconic acid, maleic acid (anhydride), vinylsulfonic acid, styrenesulfonic acid, etc.

In view of the ease in the provision of a good biocompatibility, the quantitative ratio between the polymerizable monomer and the water-soluble polyion (A) may preferably be one wherein the moles of the anionic group are equal to that of the cationic group, or one wherein the anionic group is present in excess as compared with that of the cationic group. More specifically, the mol ratio of [anionic group]/[cationic group] may preferably be in the range of 1–3, or more preferably 1.1–2. When the quantitative ratio of [anionic group]/[cationic group] is less than 1, there is strengthened a tendency that the resultant coating material becomes cationic, and the biocompatibility is decreased. On the other hand, when the quantitative ratio exceeds 3, a tendency that the solubility of the resultant coating material in the aqueous organic solvent is decreased, is strengthened.

(Monomer for Providing Water-insoluble Polymer (P))

The monomer (C) for providing the water-insoluble polymer (P) can be used without particular limitation, as long as it is soluble in the aqueous organic solvent, and it provides a polymer which is soluble in the aqueous organic solvent, and is insoluble in water.

Example of such a monomer (C) may include, e.g., (meth)acrylates such as ethyl (meth)acrylate, N-substituted (meth)acrylamides such as t-butyl (meth)acrylamide. In view of the provision of a higher water content of the aqueous organic solvent to be used as the polymerization solvent, the monomer may preferably be water-soluble. Preferred examples of such a water-soluble monomer (C) may include, e.g., 2-hydroxyethyl methacrylate and di-acetone acrylamide.

The monomer (C) for providing the water-insoluble polymer (P) may be a single monomer, but may also be a combination of plural kinds of monomers. When the combination of plural kinds of monomers is used, as long as the resultant polymer obtained by the copolymerization thereof becomes water-insoluble, it is also possible to use a monomer in combination with another monomer, even when such a monomer is one providing a water-soluble polymer by the homopolymerization thereof. For example, it is possible to use polyvinyl pyrrolidone or polyethylene glycol (meth)acrylate in the copolymerization with another monomer, even when they provide a water-soluble polymer by homopolymerization. The water-insoluble polyion (P) according to the present invention can be obtained by the copolymerization of the polymerizable monomer (B) having an electric charge of a sign opposite to that of the water-soluble polyion (A), and the monomer (C) for providing the water-insoluble polymer (P). The copolymerization ratio of monomer (B)/monomer (C) may preferably be in the range of 1–20 wt. %, more preferably 2–15 wt. % (particularly 5–10 wt. %) in terms of weight ratio. When the copolymerization ratio of monomer (B)/monomer (C) is less than 1 wt. %, the amount of the water-soluble polyion (A) to be fixed by the ionic bonding becomes insufficient and the exhibition of the function of the water-soluble polyion (A) becomes insufficient. On the other hand, the copolymerization ratio exceeds 20 wt. %, the solubility of the ion complex in the aqueous organic solvent is decreased.

(Ion Complex)

As the ion complex according to the present invention, it is possible to use only one kind of ion complex, or a mixture of a plurality of different kinds of ion complexes, as long as each is water-insoluble and is soluble in the aqueous organic solvent. For example, when an ion complex having an anticoagulant property is used in combination with an ion complex having an antibacterial property, it is possible to obtain a coating material simultaneously exhibiting an anticoagulant property and an antibacterial property.

When a mixture of plural kinds of different ion complexes is used, an insoluble ion complex can be formed in some cases, when ion complexes having signs (total sum of the electric charges in each ion complex) different from each other (i.e., polyanion and polycation) are mixed. Accordingly, it is preferred that the signs of all of the ion complexes are the same. In view of the biocompatibility thereof, the sign of the ion complex may preferably correspond to "negative electric charge", since the biocompatibility of such an ion complex is considered to be good.

More specifically, an ion complex (or coating material) comprising a mixture of different kinds of ion complexes may be obtained, e.g., by a method wherein an ion complex (negatively charged as a whole) comprising a water-insoluble polycation and a water-soluble polyanion, and an ion complex (negatively charged as a whole) comprising a water-insoluble polyanion and a water-soluble polycation are respectively dissolved in aqueous organic solvent(s), then the resultant solutions are mixed with each other, and thereafter the aqueous organic solvent is evaporated.

(Coating Method)

The ion complex or coating material according to the present invention can be used in a form which exhibit its own function. For example, the ion complex or coating material can be used as into various biomedical material in itself. However, it is also possible to locally dispose the ion complex or coating material on the surface of another material, as long as such a form allows the exhibition of the function thereof. For example, when the ion complex or coating material according to the present invention is used as a biomedical material, it is sufficient that the complex or material is locally disposed only on the surface thereof which is to be in contact with a living organism. Accordingly, the ion complex or coating material can be used as a coating disposed on the surface by a biomedical material formed from various materials (such as metals and plastics) which are to be in contact with a living organism.

The coating method usable for the complex or material of the present invention is not particularly limited. However, e.g., it is possible to preferably subject the coating material according to the present invention to coating by using a method (so-called solvent casting method) wherein a material to be coated is immersed in a solution obtained by dissolving the ion complex according to the present invention in an aqueous organic solvent, or such a solution is applied onto the material to be coated, and then the aqueous organic solvent is evaporated.

As another coating method, it is possible that the ion complex (or coating material) according to the present invention is formed into powder and is attached to a material to be coated, the powder is swollen by using an aqueous organic solvent, and thereafter the solvent is evaporated, thereby to coat the material with the ion complex. As the method for the powder formation, it is possible to mechanically crush the ion complex (or coating material) according to the present invention in a dry state, or to precipitate fine powder from a state of the ion complex or coating material dissolved in an aqueous organic solvent by changing the solvent composition or changing the temperature so as to form the ion complex or coating material into powder (chemical crushing). In order to attach the powder to a material to be coated, it is possible to moisten the material to be coated with a solvent and then attach the fine powder thereto. However, it is particularly preferred to use an electrostatic coating method, in view of the ease of forming a uniform coating.

(Coating Material)

The coating material according to the present invention comprises at least the above-mentioned ion complex comprising the water-insoluble polyion (P), and the water-soluble polyion (A). The coating material may contain another additive or a third component as desired to an extent in which the additive or third component does not substantially obstruct the function of the ion complex.

Examples of such an additive or third component may include, e.g., a component for imparting a lubricating property to the surface of the coating (such as Teflon particles), a component for imparting an abrasion resistance to the coating layer (such as metal powder), a component for imparting a flexibility to the coating layer (such as plasticizer), etc.

(Coated Product)

The ion complex or coating material according to the present invention can be used in the form of a coating on various base materials or substrates, as desired. The kind of material, configuration, surface condition of such base materials or substrates are not particularly limited, as long as these materials or substrates can be coated with the ion complex or coating material according to the present invention. Examples of such kind of material may include metals, plastics, ceramics, composite materials, etc. Examples of the abovementioned configuration may include a sheet form, powder or particles, fiber shape, a cylindrical shape (solid or hollow, such as catheter configuration), a net shape (such as stent configuration). Further, examples of the above-mentioned surface condition may include an uneven surface (a roughened surface), a smooth surface, and combinations thereof, etc.

When the ion complex or coating material according to the present invention is used as a biomedical material, as described above, it is sufficient that the ion complex or coating material is selectively present on the surface to be in contact with a living organism, in a localized or dotted form.

Hereinbelow, the present invention will be described in more detail with reference to Examples.

EXAMPLE 1

2.0 g of di-acetone acrylamide (DACAM, mfd. by Kyowa Hakko K.K.), 0.14 g of polyethylene glycol monomethacrylate (PME4000, average molecular weight 4,000, mfd. by Nippon Yushi K.K.), 0.19 g of a 75% aqueous solution of methyl chloride-quaternarized product of N,N-dimethylaminopropyl acrylamide (DMAPAAQ (aq), mfd. by Kojin K.K.) and 0.14 g of heparin sodium (mfd. by Wako Junyaku K.K.) were dissolved in 7.5 g of distilled water.

After each of the above-mentioned components was uniformly dissolved, 6 g of ethanol was added to the resultant mixture, and under a nitrogen stream, 0.2 ml of a 10 wt. %-aqueous ammonium persulfate (APS) solution and 20 $\mu$l of N,N,N',N'-tetramethyl ethylenediamine (TEMED) were added thereto, and the resultant mixture was subjected to a reaction at room temperature (25° C.) for two hours. The thus obtained transparent viscous solution was evaporated to dryness by using an evaporator. The resultant residue was sufficiently washed with distilled water (three times with 100 ml of distilled water), and thereafter 50 ml of ethanol was added thereto so as to dissolve the residue, and then the resultant solution was evaporated to dryness by using an evaporator. The resultant residue was sufficiently washed with distilled water, and thereafter the residue was again sufficiently washed with distilled water (three times with 100 ml of distilled water), and the resultant product in a water-containing state thereof was freeze-dried, thereby to obtain 2.4 g of coating material (1) comprising an ion complex according to the present invention.

The above-mentioned coating material (1) was insoluble in distilled water and insoluble in ethanol, but was soluble in an aqueous ethanol. When 0.2 g of the coating material (1) was dissolved in 2.3 g of aqueous ethanol (water content 18 wt. %), the coating material was completely dissolved therein so as to be converted into a transparent viscous solution (concentration of coating material (1): 8 wt. %).

About 1.6 ml of the solution (8 wt. %) of the coating material (1) was applied onto a polyurethane sheet (5 cm×5 cm, thickness 1 mm) as a material to be coated and then the solvent was evaporated. When the coating amount of the coating material (1) was determined from the increase in weight of the coated polyurethane sheet after the vacuum drying, it was found to be 125 mg (coating thickness: about 50 $\mu$m). When the water content of the coating layer was determined from the increase in weight of the coated product after the immersion thereof in distilled water at 37° C. for 24 hours, it was found to be 36 wt. %. Further, when the coating amount was again determined from the weight measurement of this product after vacuum drying, it was found that the measured value remained at 125 mg, and no change was observed therein.

EXAMPLE 2

2.0 g of di-acetone acrylamide (DACAM, mfd. by Kyowa Hakko K.K.), 0.14 g of polyethylene glycol monomethacrylate (PME4000, average molecular weight 4,000, mfd. by Nippon Yushi K.K.), 0.19 g of a 75% aqueous solution of methyl chloride-quaternarized product of N,N-dimethylaminopropyl acrylamide (DMAPAAQ (aq), mfd. by Kojin K.K.) and 0.28 g of heparin sodium (mfd. by Wako Junyaku K.K.) were dissolved in 9 g of distilled water.

After each of the above-mentioned components was uniformly dissolved, 5 g of ethanol was added to the resultant mixture and under a nitrogen stream, 0.2 ml of a 10 wt. %-aqueous ammonium persulfate (APS) solution and 20 $\mu$l of N,N,N',N'-tetramethyl ethylenediamine (TEMED) were added thereto, and the resultant mixture was subjected to a reaction at room temperature (25° C.) for two hours. The thus obtained white turbid viscous solution was evaporated to dryness by using an evaporator. The resultant residue was sufficiently washed with distilled water (three times with 100 ml of distilled water), and thereafter 50 ml of ethanol was added to the residue so as to dissolve the residue, and then the resultant solution was evaporated to dryness by using an evaporator. The resultant residue was sufficiently washed with distilled water, and thereafter the residue was again sufficiently washed with distilled water (three times with 100 ml of distilled water), and the resultant product, in a water-containing state thereof, was freeze-dried, thereby to obtain 2.5 g of coating material (2) according to the present invention.

The above-mentioned coating material (2) was insoluble in distilled water and was insoluble in ethanol, but was soluble in an aqueous ethanol. When 0.2 g of the coating material (2) was dissolved in 2.3 g of aqueous ethanol (water content 33 wt. %), the coating material was completely dissolved therein so as to be converted into a transparent viscous solution (concentration of coating material (2): 8 wt. %).

About 1.6 ml of the solution (8 wt. %) of the coating material (2) was applied onto a polyurethane sheet (5 cm×5 cm, thickness 1 mm) and then the solvent was evaporated. When the coating amount of the coating material (2) was determined from the increase in weight of the coated polyurethane sheet after the vacuum drying, it was found to be 125 mg (coating thickness: about 50 $\mu$m). When the water content of the resultant coating layer was determined from the increase in weight of the coated product after the immersion thereof in distilled water at 37° C. for 24 hours, it was found to be 42 wt. %. Further, when the coating amount was again determined from the weight measurement of this product after vacuum drying, it was found that the coating amount remained at 125 mg, and no change was observed therein.

EXAMPLE 3

2.0 g of di-acetone acrylamide (DACAM, mfd. by Kyowa Hakko K.K.), 0.19 g of a 75% aqueous solution of methyl chloride-quaternarized product of N,N-dimethylaminopropyl acrylamide (DMAPAAQ (aq), mfd. by Kojin K.K.) and 0.28 g of heparin sodium (mfd. by Wako Junyaku K.K.) were dissolved in 9 g of distilled water.

After each of the above-mentioned components was uniformly dissolved, 5 g of ethanol was added to the resultant mixture, and under a nitrogen stream, 0.2 ml of a 10 wt. %-aqueous ammonium persulfate (APS) solution and 20 µl of N,N,N',N'-tetramethyl ethylenediamine (TEMED) were added thereto, and the resultant mixture was subjected to a reaction at room temperature (25° C.) for two hours. The thus obtained white turbid gel-like product was evaporated to dryness by using an evaporator. The resultant residue was sufficiently washed with distilled water (three times with 100 ml of distilled water), and thereafter 50 ml of ethanol was added to the residue so as to dissolve the residue, and then the resultant solution was evaporated to dryness by using an evaporator. The resultant residue was sufficiently washed with distilled water, and thereafter the residue was again sufficiently washed with distilled water (three times with 100 ml of distilled water), and the resultant product, in a water-containing state thereof, was freeze-dried, thereby to obtain 2.3 g of coating material (3) according to the present invention.

The above-mentioned coating material (3) was insoluble in distilled water and was insoluble in ethanol, but was soluble in an aqueous ethanol. When 0.2 g of the coating material (3) was dissolved in 2.3 g of aqueous ethanol (water content 33 wt. %), the coating material was completely dissolved therein so as to be converted into a transparent viscous solution (concentration of coating material (3): 8 wt. %).

About 1.6 ml of the solution (8 wt. %) of the coating material (3) was applied onto a polyurethane sheet (5 cm×5 cm, thickness 1 mm) and the solvent was evaporated. When the coating amount of the coating material (3) was determined from the increase in weight of the coated polyurethane sheet after the vacuum drying, it was found to be 125 mg (coating thickness: about 50 µm). When the water content of the coating layer was determined from the increase in weight of the coated product after the immersion thereof in distilled water at 37° C. for 24 hours, it was found to be 40 wt. %. Further, when the coating amount was again determined from the weight measurement of this product after vacuum drying, it was found that the coating amount remained at 125 mg, and no change was observed therein.

EXAMPLE 4

1.6 g of di-acetone acrylamide (DACAM, mfd. by Kyowa Hakko K.K.), 0.19 g of a 75% aqueous solution of methyl chloride-quaternarized product of N,N-dimethylaminopropyl acrylamide (DMAPAAQ (aq), mfd. by Kojin K.K.) and 0.20 g of heparin sodium (mfd. by Wako Junyaku K.K.) were dissolved in 8.5 g of distilled water.

After each of the above-mentioned components was uniformly dissolved, a solution obtained by dissolving 0.40 g of ethyl acrylate (mfd. by Wako Junyaku K.K.) in 5 g of ethanol was added to the resultant mixture, and under a nitrogen stream, 0.2 ml of a 10 wt. %-aqueous ammonium persulfate (APS) solution and 20 µl of N,N,N',N'-tetramethyl ethylenediamine (TEMED) were added thereto, and the resultant mixture was subjected to a reaction at room temperature (25° C.) for two hours. The thus obtained white turbid gel-like product was evaporated to dryness by using an evaporator. The resultant residue was sufficiently washed with distilled water (three times with 100 ml of distilled water), and thereafter 50 ml of ethanol was added to the residue so as to dissolve the residue, and then the resultant solution was evaporated to dryness by using an evaporator. The resultant residue was sufficiently washed with distilled water, and thereafter the residue was again sufficiently washed with distilled water (three times with 100 ml of distilled water), and the resultant product in a water-containing state thereof was freeze-dried, thereby to obtain 2.2 g of coating material (4) according to the present invention.

The above-mentioned coating material (4) was insoluble in distilled water and was insoluble in ethanol, but was soluble in an aqueous ethanol. When 0.2 g of the coating material (4) was dissolved in 2.3 g of aqueous ethanol (water content 18 wt. %), the coating material was completely dissolved therein so as to be converted into a transparent viscous solution (concentration of coating material (4): 8 wt. %).

About 1.6 ml of the solution (8 wt. %) of the coating material (4) was applied onto a polyurethane sheet (5 cm×5 cm, thickness 1 mm) and the solvent was evaporated. When the coating amount of the coating material (4) was determined from the increase in weight of the coated polyurethane sheet after the vacuum drying, it was found to be 125 mg (coating thickness: about 50 µm). When the water content of the coating layer was determined from the increase in weight of the coated product after the immersion thereof in distilled water at 37° C. for 24 hours, it was found to be 37 wt. %. Further, when the coating amount was again determined from the weight measurement of this product after vacuum drying, it was found that the coating amount remained at 125 mg, and no change was observed therein.

When the above-mentioned polyurethane sheet which had been coated with the coating material (4) was immersed in a 0.006%-aqueous Toluidine Blue solution for one hour and then washed with water, the polyurethane sheet which had been coated with the coating material (4) was dyed in purple. That is, it was confirmed that the free anionic group of heparin (sulfonic acid group) was present in excess, as compared with the cationic group (quaternary amine).

EXAMPLE 5

(Anticoagulant Property Test)

The solution of the coating material (4) (concentration of coating material (4): 8 wt. %) in aqueous ethanol (water content 18 wt. %) which had been obtained in Example 4 was circulated in the inside of a vinyl chloride tube (inside diameter 3 mm, outside diameter 6 mm) at a flow rate of 2 ml/minute using a Perista-pump (roller pump). Then, nitrogen gas was passed through the tube at a flow rate of 10 ml/minute to effect aeration and drying, thereby to coat the inside of the tube with the coating material.

The resultant tube was sufficiently washed with distilled water, and then the tube was cut so as to provide a length of 80 cm. By using the resultant tube, an adult beagle dog was subjected to an operation so as to form a by-pass between the arteria femoralis and the vena femoralis thereof (A-V shunt method). When the coated tube obtained in this Example was used, no thrombus formation therein was observed for at least three hours counted from the initiation of the experiment. On the contrary, when the same experiment was repeated except for using a non-coated vinyl chloride tube, blood coagulation occurred in the tube and thrombus formation therein was observed at about one hour counted from the initiation of the experiment.

EXAMPLE 6

1.6 g of di-acetone acrylamide (DACAM, mfd. by Kyowa Hakko K.K.), 0.07 g of sodium acrylate (mfd. by Wako Junyaku K.K.) and 0.20 g of polymyxin-B sulfate (mfd. by Wako Junyaku K.K.) were dissolved in 8.5 g of distilled water.

After each of the above-mentioned components was uniformly dissolved, a solution obtained by dissolving 0.40 g of ethyl acrylate (mfd. by Wako Junyaku K.K.) in 5 g of ethanol was added to the resultant mixture, and under a nitrogen stream, 0.2 ml of a 10 wt. %-aqueous ammonium persulfate (APS) solution and 20 µl of N,N,N',N'-tetramethyl ethylenediamine (TEMED) were added thereto, and the resultant mixture was subjected to a reaction at room temperature (25° C.) for two hours. The thus obtained white turbid gel-like product was evaporated to dryness by using an evaporator. The resultant residue was sufficiently washed with distilled water (three times with 100 ml of distilled water), and thereafter 50 ml of ethanol was added to the residue so as to dissolve the residue, and then the resultant solution was evaporated to dryness by using an evaporator. The resultant residue was sufficiently washed with distilled water, and thereafter the residue was again sufficiently washed with distilled water (three times with 100 ml of distilled water), and the resultant product, in a water-containing state thereof, was freeze-dried, thereby to obtain 2.2 g of coating material (5) according to the present invention.

The above-mentioned coating material (5) was insoluble in distilled water and was insoluble in ethanol, but was soluble in an aqueous ethanol. When 0.2 g of the coating material (5) was dissolved in 2.3 g of aqueous ethanol (water content 18 wt. %), the coating material was completely dissolved therein so as to be converted into a transparent viscous solution (concentration of coating material (5): 8 wt. %).

About 1.6 ml of the solution (8 wt. %) of the coating material (5) was applied onto a polyurethane sheet (5 cm×5 cm, thickness 1 mm) and then the solvent was evaporated. When the coating amount of the coating material (5) was determined from the increase in weight of the coated polyurethane sheet after the vacuum drying, the coating amount was found to be 125 mg (coating thickness: about 50 $\mu$m). When the water content of the coating layer was determined from the increase in weight of the coated product after the immersion thereof in distilled water at 37° C. for 24 hours, it was found to be 37 wt. %. Further, when the coating amount was again determined from the weight measurement of this product after vacuum drying, it was found that the coating amount remained at 125 mg, and no change was observed therein.

EXAMPLE 7
(Antibacterial Property Test)

The polyurethane sheet coated with the coating material (5) which had been obtained in Example 6 was cut into a disc shape having a diameter of 1 cm, and the above-mentioned coated surface thereof was pressed onto a DHL agar flat-plate culture medium (Difco Plate Agar) with which *E. coli* (*E. coli*, ATCC 25922) had been inoculated, by using a sterilized forceps so as to dispose the disc on the culture medium.

In such a state, the above culture medium was subjected to culturing at 32–35° C. overnight (for about 24 hours), a zone corresponding to the growth inhibition of the bacteria (with a width of about 2 mm) was observed in the circumference of the disc-shaped sheet comprising the polyurethane sheet, and the antibacterial activity of the above-mentioned coating material was confirmed.

EXAMPLE 8

1.7 g of di-acetone acrylamide (DACAM, mfd. by Kyowa Hakko K.K.), 0.26 g of sodium styrenesulfonate (mfd. by Wako Junyaku K.K.) and 0.05 g of dibekacin sulfate (dibekacin, mfd. by Meiji Seika K.K.) as a kanamycin-type semi-synthetic antibiotic were dissolved in 1.3 g of distilled water.

After each of the above-mentioned components was uniformly dissolved, a solution obtained by dissolving 0.6 g of ethyl acrylate (mfd. by Wako Junyaku K.K.) in 1.0 g of dimethylformamide (mfd. by Wako Junyaku K.K.) was added to the resultant mixture, and under a nitrogen stream, 0.2 ml of a 10 wt. %-aqueous ammonium persulfate (APS) solution and 20 $\mu$l of N,N,N',N-tetramethyl ethylenediamine (TEMED) were added thereto, and the resultant mixture was subjected to a reaction at room temperature (25° C.) for two hours. 10 g of dimethylformamide was added to the thus obtained reaction mixture and the reaction mixture was completely dissolved therein, thereby to prepare a coating solution.

The coating solution was subjected to solvent casting on a polyethylene film at room temperature (25° C.) and dried at room temperature for 24 hours, and then the resultant coating was peeled from the polyethylene film, thereby to prepare a composition film (dimension 5 cm×5 cm, thickness about 70 $\mu$m).

The resultant product was immersed in a large amount (about 2 liters) of physiological saline at room temperature for night and day to remove the unreacted monomer and the unreacted dibekacin sulfate, and then the product was dried under vacuum, thereby to prepare a composition film to which dibekacin sulfate had been bonded. The composition film was insoluble in distilled water and was insoluble in ethanol, but was soluble in an aqueous ethanol.

EXAMPLE 9
(Antibacterial Property Test)

The coated film obtained in Example 8 was cut into a rectangular shape having a side of about 0.5 cm, and then was immersed in a large amount (about 1000 ml) of physiological saline at room temperature for respective periods of time (30 minutes, 3 hours, 8 hours, one day, 3 days, one week, two weeks, and 26 days). Thereafter, the above-mentioned coated surface of the film was pressed onto a DHL agar flat-plate culture medium (Difco Plate Agar) with which *Bacillus subtilis* had been inoculated, by using a sterilized forceps so as to dispose the film on the culture medium.

In this state, the culture medium was subjected to culturing at 32–35° C. overnight (for about 24 hours), and the width of a zone corresponding to the growth inhibition of bacteria to be formed in the circumference of the film was measured, thereby to measure the influence of the operations for immersing the film in a large amount of physiological saline for the respective periods of time, on the antibacterial activity of the film.

As a result, the film after the immersion for 26 days showed a width of the growth inhibition zone which was about 86% of the film without immersion (control, growth inhibition zone=about 25 mm). That is, it was confirmed that the antibacterial property of the above film was maintained for a long period of time even in a large amount of physiological saline (i.e., in an environment similar to that in a body of an animal such as a human).

As described hereinabove, according to the present invention, there is provided an ion complex comprising a water-insoluble polyion (P) and a water-soluble polyion (A); the ion complex being insoluble in water and soluble in an aqueous organic solvent.

The present invention also provides a coated product comprising a material to be coated, and a coating layer covering at least a portion of the surface of the material to be coated, wherein the coating layer comprises an ion complex which comprises a water-insoluble polyion (P) and a water-soluble polyion (A); and is insoluble in water and soluble in an aqueous organic solvent.

The present invention further provides a coating method comprising:

forming on a material to be coated a layer of a solution comprising an aqueous organic solvent and an ion complex dissolved in the solvent; and evaporating the aqueous organic solvent to form on the material to be coated a coating layer comprising the ion complex;

wherein the ion complex comprises a water-insoluble polyion (P) and a water-soluble polyion (A); and the ion complex is insoluble in water and soluble in an aqueous organic solvent.

The present invention further provides a coating method comprising:

attaching a coating material in the form of powder comprising an ion complex to a material to be coated;

swelling the ion complex with an aqueous organic solvent; and evaporating the aqueous organic solvent to form on the material to be coated a coating layer comprising the ion complex;

wherein the ion complex comprises a water-insoluble polyion (P) and a water-soluble polyion (A); and the ion complex is insoluble in water and soluble in an aqueous organic solvent.

The above-mentioned ion complex comprising a water-soluble polyion (A) and a water-insoluble polyion (P) according to the present invention is soluble in an aqueous organic solvent. Accordingly, such an ion complex can easily be subjected to coating (such as solvent casting) for various base materials or substrates, and is applicable to the surface of a wide range of base materials or substrates (such as medical devices) comprising various materials.

In addition, the problems encountered in the conventional coating material (e.g., heparinized material) are solved by utilizing the ion complex according to the present invention. In other words, a water-soluble polyion (A) such as polyanion (e.g., heparin) having an anticoagulant property, and a polycation (e.g., polymyxin B) having an antibacterial property can be electrostatically fixed stably into the surface layer of various base materials or substrates (such as medical devices).

Further, when the coating surface comes into contact with a body fluid such as blood, it is possible to slowly release the water-soluble polyion (A). (such as polyanion having an anticoagulant property and polycation having an antibacterial property) into the body fluid, while effectively suppressing the dissolution of the component of the coating other than the water-soluble polyion (A).

In the ion complex according to the present invention, the water-soluble polyion (A) forms a (poly)ion complex with the water-insoluble polyion (P), and therefore the dissolution of the water-soluble polyion can be relatively suppressed, whereby the function of the complex (e.g., biological activity thereof) can also be sustained stably for a long period of time.

Further, in the ion complex according to the present invention, an ion complex of the water-soluble polyion (A) and the water-insoluble polyion (P) is formed in advance, and therefore it is possible to control the quantity of the functional material in the ion complex (polyion (A) and/or polyion (P); e.g., biologically active substance) precisely and arbitrarily.

Further, according to the coating method of the present invention, the surface of various base materials or substrates can be easily coated with the above-mentioned ion complex.

What is claimed is:

1. An ion complex comprising a water-insoluble polyion (P) and a water-soluble polyion (A); the ion complex being insoluble in water and soluble in an aqueous organic solvent.

2. An ion complex according to claim 1, wherein at least one of the polyions (P) and (A) is a polyion having a biological activity.

3. An ion complex according to claim 1, wherein either one of the polyions (P) and (A) is a polycation, and the other is a polyanion.

4. An ion complex according to claim 1, wherein the ion complex is an ion complex which has been obtained by copolymerizing a polymerizable monomer (B) having an electric charge of a sign opposite to that of the polyion (A), with a monomer (C) providing the water-insoluble polymer (P), in the co-presence of the water-soluble polyion (A) dissolved in an aqueous organic solvent.

5. An ion complex according to claim 1, which has a characteristic such that the water-soluble polyion (A) constituting the ion complex is slowly released into an aqueous fluid when the ion complex comes into contact with the aqueous fluid.

6. An ion complex according to claim 1, wherein the polyion (A) is a polyanion comprising an anticoagulant.

7. An ion complex according to claim 6, wherein the anticoagulant comprises heparin.

8. An ion complex according to claim 1, which is substantially insoluble in an organic solvent.

9. A coated product comprising a material to be coated, and a coating layer covering at least a portion of the surface of the material to be coated, wherein the coating layer comprises an ion complex which comprises a water-insoluble polyion (P) and a water-soluble polyion (A); and is insoluble in water and soluble in an aqueous organic solvent.

10. A coated product according to claim 5, wherein the ion complex has a characteristic such that the water-soluble polyion (A) constituting the ion complex is slowly released into an aqueous fluid when the ion complex comes into contact with the aqueous fluid.

11. A coated product according to claim 9, wherein the ion complex is substantially insoluble in an organic solvent.

12. A coating method comprising:

applying a solution comprising an aqueous organic solvent and an ion complex dissolved in the solvent on a material to be coated; and evaporating the aqueous organic solvent to form a coating on the material to be coated;

wherein the ion complex comprises a water-insoluble polyion (P) and a water-soluble polyion (A); and the ion complex is insoluble in water and soluble in an aqueous organic solvent.

13. A coating method according to claim 12 wherein the ion complex has a characteristic such that the water-soluble polyion (A) constituting the ion complex is slowly released into an aqueous fluid when the ion complex comes into contact with the aqueous fluid.

14. A coating method comprising:

attaching at least an ion complex in the form of powder to a material to be coated;

swelling the ion complex with an aqueous organic solvent; and evaporating the aqueous organic solvent to form a coating;

wherein the ion complex comprises a water-insoluble polyion (P) and a water-soluble polyion (A); and the ion complex is insoluble in water and soluble in an aqueous organic solvent.

15. A coating method according to claim 14, wherein the ion complex has a characteristic such that the water-soluble polyion (A) constituting the ion complex is slowly released into an aqueous fluid when the ion complex comes into contact with the aqueous fluid.

* * * * *